United States Patent [19]

Grim

[11] Patent Number: 4,913,755
[45] Date of Patent: Apr. 3, 1990

[54] METHOD OF FORMING ORTHOPAEDIC GEL PADS

[75] Inventor: Tracy E. Grim, Broken Arrow, Okla.

[73] Assignee: Royce Medical Company, Westlake Village, Calif.

[21] Appl. No.: 168,681

[22] Filed: Mar. 16, 1988

[51] Int. Cl.$^4$ .................... B32B 31/16; B32B 31/18
[52] U.S. Cl. ................................ 156/145; 156/245; 156/285; 156/300; 128/80 H; 128/89 R; 128/166; 425/388; 264/516
[58] Field of Search ................ 128/80 H, 89 R, 166; 156/285, 145, 299, 300, 245; 425/388; 264/516, 510

[56] References Cited

U.S. PATENT DOCUMENTS

| | | | |
|---|---|---|---|
| 3,322,598 | 5/1967 | Marks et al. | 264/516 X |
| 3,997,052 | 12/1976 | Eddy et al. | 264/510 X |
| 4,114,213 | 9/1978 | Beernaerts et al. | 156/285 X |
| 4,116,736 | 9/1978 | Sanson et al. | 156/285 X |
| 4,454,871 | 6/1984 | Mann et al. | 128/89 R |
| 4,628,945 | 12/1986 | Johnson, Jr. | 128/80 HX |
| 4,637,789 | 1/1987 | Netznik | 425/388 X |
| 4,671,267 | 6/1987 | Stout | 128/155 X |

Primary Examiner—Robert A. Dawson
Assistant Examiner—Michele K. Yoder
Attorney, Agent, or Firm—Poms, Smith, Lande & Rose

[57] ABSTRACT

A method for forming gel-filled cushion pads that provide a resilient support against the ankle, comprises the use of a vacuum chamber substantially covered at the top with a perforated base plate. A thin, rubber foam layer spacer pad with openings is overlaid on the base plate. A thin, rubber foam layer front pad with openings is overlaid on the spacer pad in alignment with the spacer pad openings. Adhesive material is coated on the top surface of the front pad. A thin layer of urethane is overlaid on the adhesive coated upper surface of the front pad and vacuum is applied to pull the urethane layer toward the base plate. With the urethane layer substantially conformed to the inner walls of these pads, a patterned pocket is formed for receiving liquid gel. Then, a predetermined amount of liquid gel is poured into this pocket and allowed to cool and solidify to form a dense semi-solid gel. A rubber foam back pad covered with adhesive material on its bottom surface is then overlaid onto the urethane layer to enclose the gel material between the urethane film, and the back pad. The assembly comprising the back pad, gel layers, front pad, and urethane layer is removed from the base plate. Because each front pad may include several patterned opening on its surface, several contiguous units of gel-filled cushion pads may be formed in this process and cut accordingly.

17 Claims, 2 Drawing Sheets

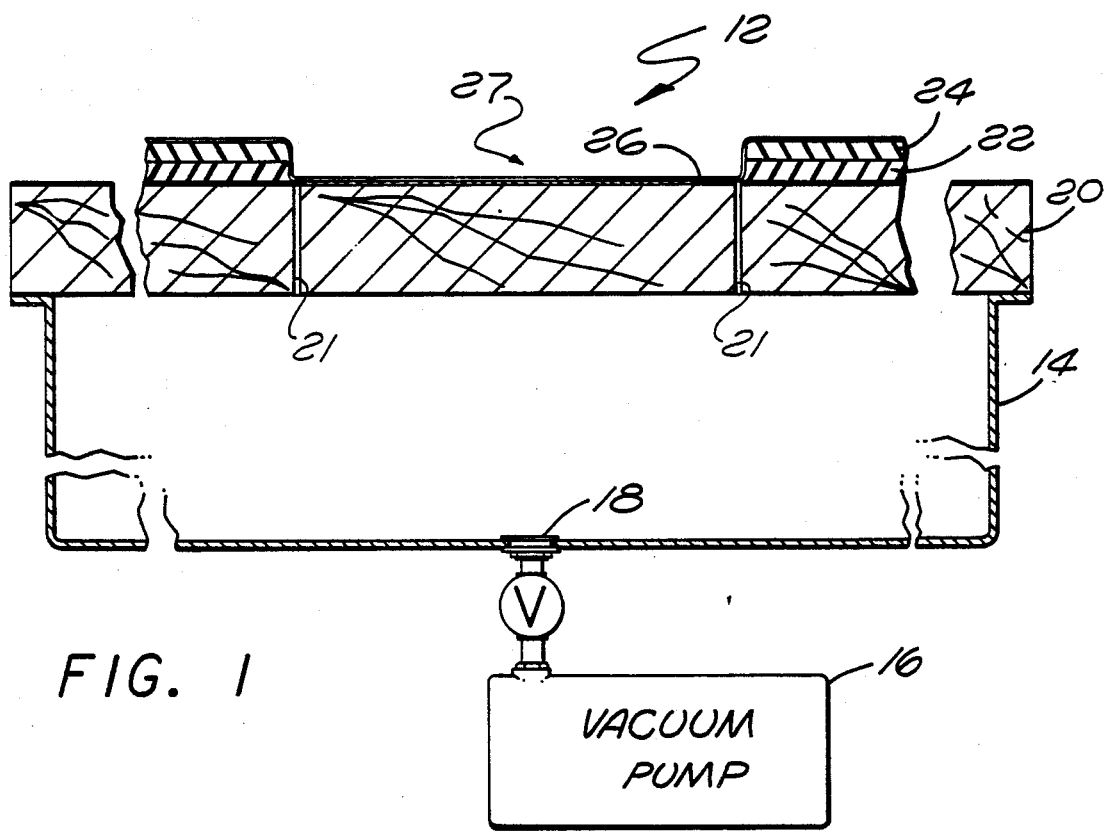
FIG. 1
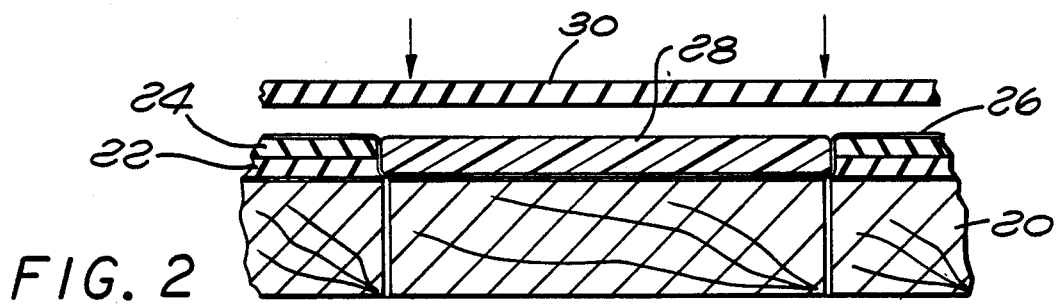
FIG. 2
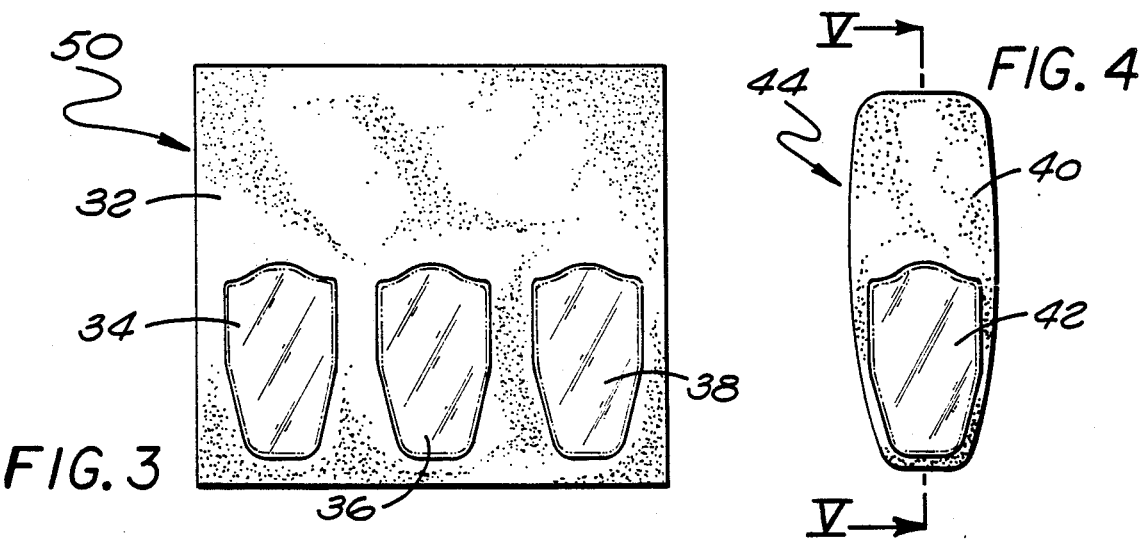
FIG. 3
FIG. 4

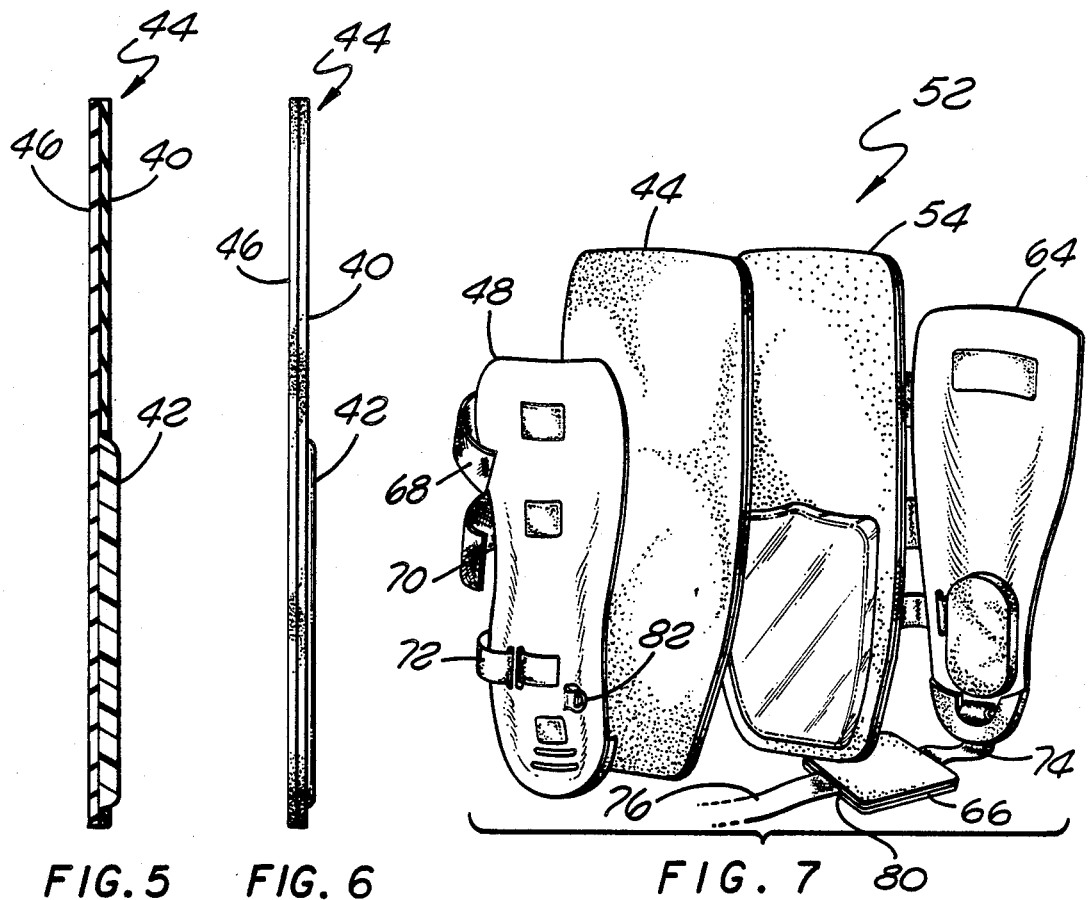
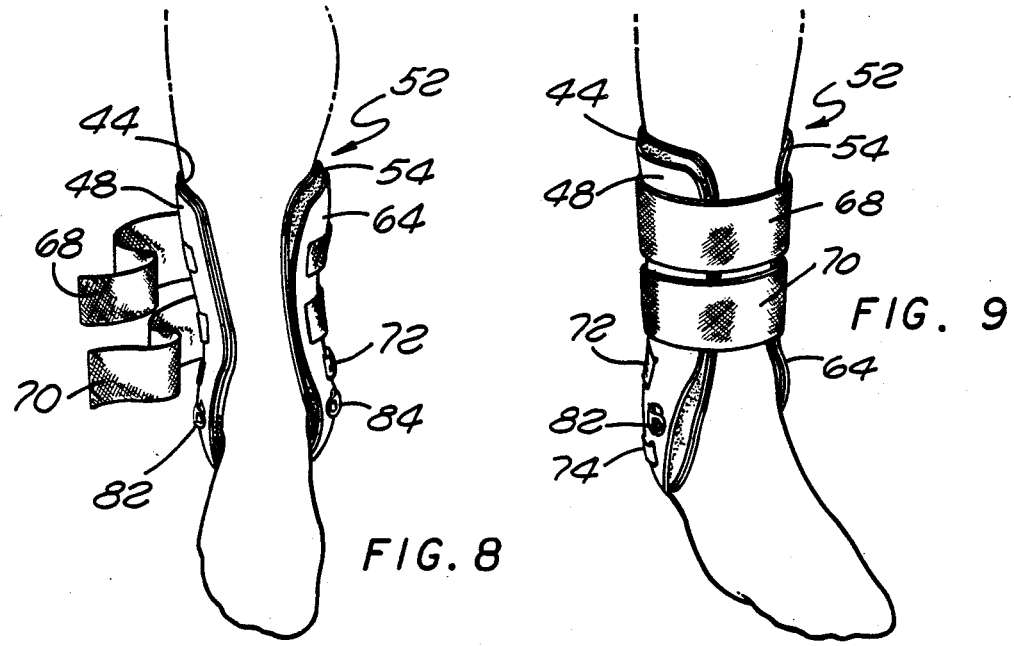

METHOD OF FORMING ORTHOPAEDIC GEL PADS

RELATED PATENT APPLICATIONS

Attention is directed to U.S. Pat. Application Ser. No. 055,711, filed May 29, 1987, now U.S. Pat. No. 4,844,094, entitled "Ankle Brace" and assigned to the assignee of this application.

BACKGROUND OF THE INVENTION

After injury to an ankle, such as a fracture or severe ankle sprain, it may be necessary to completely immobilize the ankle through the use of a molded plaster or resin cast. However, once the injury has been stabilized, recovery may be hastened by removing the molded plaster or resin cast and using a removable functional walking brace so that the ankle can be exercised during healing.

An important element of these functional walking braces is the liner element that provides a resilient support against the sides of the ankle. The liner helps stabilize the ankle against inversion and eversion while still permitting the normal dorsi-flexion and plantarflexion movement of the ankle. It has previously been proposed to form such pads of foam rubber, or using inflatable bags.

One such proposed prior ankle brace using an air-inflatable liner is shown in prior U.S. Pat. No. 4,280,489 listing Glen W. Johnson, Jr. as the inventor. Although the air-inflatable liner provides some resilient support against the ankle, it suffers from the following disadvantages. One disadvantage is that the air is unduly buoyant, and permits rapid movement of the air from one side to another, so that adequate support is not provided. Further, with air inflatable bladders, a puncture renders the braces inoperative and dangerous to the user as the outer rigid plastic shells could cut or rub the wearer.

The use of foam rubber pad, as a liner in walking braces is disclosed in U.S. Pat. No. 4,572,169 listing Maullin and Jones as inventors. The use of foam rubber has significant disadvantages in that the foam rubber is U.V. sensitive, and tends to deteriorate after a certain period of time. In addition, the open cells in the foam material collect moisture, such as sweat, with the undesired bacterial growth and odor. No such result can occur with gel pads. Further, the foam does not tend to conform to the configuration of the ankle joint, but bounces back to its original configuration. Also, neither air filled cushioning arrangements nor foam are suitable for hot and cold temperature therapy.

Accordingly, the objects of this invention include providing a walking brace liner that provides a resilient support against the ankle that is free from adverse effects of puncturing, lasts long and does not deteriorate in U.V. light, forms a relatively stable pad, conforms to the configuration of the ankle, has a high thermal capacity, has well defined boundaries, has homogeneous thickness throughout its length and width, and is very comfortable when used for therapeutic heating or chilling of the injured leg.

SUMMARY OF THE INVENTION

The present invention is directed to a method and an apparatus for forming gel-filled cushion pads that provide a resilient support against the ankle. The apparatus includes, among other elements, a vacuum chamber that is substantially enclosed except at the top. A perforated plate having many drilled, small holes on its surface is used to cover the top portion of the vacuum chamber. The vacuum chamber also includes a channel for connecting it to a vacuum pump. A vacuum pump is used to withdraw the air from the vacuum chamber.

A spacer pad, normally made of foam rubber, is then laid over the perforated plate. The spacer pad normally includes one or more openings on its surface. Each of these openings provide for a space that has the perforated base plate as its base and has a depth equal to the thickness of the spacer pad. Further, the walls of this space have the pattern of the corresponding opening on the surface of spacer pad.

The present invention also includes a front aperture pad that is normally made of rubber foam, and overlies the space pad. The front aperture pad also has openings on its surface that normally have the same pattern as the openings on the surface of the spacer pad. The front aperture pad is normally laid over on the spacer pad such that these openings on the spacer pad are in alignment with openings on the spacer pad on that pad. With the openings on the aperture pad and spacer pad aligned, a laterally enclosed space is formed. This space is laterally confined at the bottom by the perforated base plate, and is laterally confined by the inner walls of the spacer pad and front pad. The depth of this space is substantially equal to the sum of one thickness of the spacer pad and one thickness of the front pad. This space, hereinafter called "the gel-space" is used for storing the liquid gel for the solidification process.

Another element of the apparatus is a thin plastic film that is normally made of urethane. With the front pad in alignment with the spacer pad, an adhesive coating is located on the upper surface of the front pad and a thin film of urethane is laid over the front pad. Then, the vacuum pump is turned on, causing air to be drawn from the vacuum chamber. The fine perforations through the base plate extend to the aligned openings in the two pads within the periphery of these openings. As a result, a stream of air flows into the vacuum chamber through the exposed holes on the surface of the perforated base plate. The inflow of air through these holes causes the thin film to be drawn towards the perforated plate tightly and neatly particularly around the edges of the gel-receiving openings. Concurrently with this vacuuming process, a heating device is used to raise the temperature of the thin film and thereby cause it to expand and snugly cover the exposed base plate as well as the walls of the gel-space. After the heating process, the thin film substantially forms the boundaries of the gel-space. A predetermined amount of the gel is then mixed so that it will solidify in a few minutes, and is poured into the gel-space, on top of the thin film, and allowed to solidify for a few minutes. The predetermined amount of gel is measured to substantially fill the gel-space. The vacuum process may continue while the liquid gel is being poured into the gel-space to make sure that the thin film will not be substantially displaced.

After the gel has solidified, an adhesive coated back pad, normally made of foam rubber, is laid over on top of the thin plastic film.

With this process, a solid, dense layer of gel is confined between the back pad on the top and the thin film at the bottom, with the thin film being secured to the inner walls of the spacer pad and front pad. Each one of the gel filled gel-spaces constitutes a gel pad unit. Since several contiguous gel-spaces may be formed by overlying the front pad on the spacer pad, the above process may involve formation of several contiguous gel pad units.

Since a number of contiguous gel pad units may be formed concurrently during the above process, these gel pad units may be cut out to form a single unit. Each individual unit of these gel cushion pads or liners may then be used in walking braces for providing a resilient support against the ankle. By using these gel liners for each walking brace, multiple advantages are realized.

First, a gel cushion pad may be repeatedly punctured with no adverse effect, as the gel seals itself and does not leak out. Further these gel liners form a relatively stable pad in which the gel does shift in position somewhat to conform to the configuration of the ankle bone, but does not migrate more than about one-quarter or one inch.

In addition, gel liners produced by the method of the present invention have a well defined boundary and homogeneous thickness throughout the length and width of the gel pad. Further, since the gel pad covers only the injured part of the leg, the rest of the leg will not be unnecessarily affected by the heat and cold therapeutic treatment received by the injured part of the leg.

It is further noted that the gel pads may be formed by the method of the present invention, using a somewhat thicker spacer pad, and having a backing in the form of an additional urethane film or layer, heat sealed or adhered to the underlying urethane layer to form a simple urethane film covered layer, similar to that shown in the prior copending patent application cited hereinabove.

In accordance with another aspect of the invention, an orthopaedic assembly includes a gel pad employed in combination with stiff supporting arrangements for splinting a bone or joint, with the gel pad being secured to the stiff supporting arrangements to match the irregular and individual configuration of the joint or bone to which the orthopaedic assembly is to be secured. These arrangements are applicable to the wrist, knee, and other bones or joints, as well as to the ankle.

Other objects, features, and advantages of the invention will become apparent from a consideration of the following detailed description and from the accompanying drawings.

BRIEF DESCRIPTION OF THE DRAWINGS

FIG. 1 is a cross-sectional view of an apparatus for forming gel-filled cushion pad or liners, illustrating the principles of the invention;

FIG. 2 is a partial cross-sectional side view of the apparatus of FIG. 1, further illustrating the formation of the gel-pads;

FIG. 3 is a top view of the finished product that includes three contiguous units of gel pad liners;

FIG. 4 is a top view of an individual gel-pad unit that is cut out of the finished product shown in FIG. 3;

FIG. 5 is a cross-sectional view taken along the line V—V of FIG. 4, illustrating the back pad, front aperture pad, and the semi-solid gel layer;

FIG. 6 is a side view of the gel pad of FIG. 4, illustrating the manner in which the gel pad is confined to the back pad, and inner walls of the front pad;

FIG. 7 is a perspective view of a walking brace assembly, illustrating the manner in which the individual units of gel-pads are used in the walking brace;

FIG. 8 illustrates the manner in which the gel pads and the walking brace support the ankle;

FIG. 9 illustrates the manner in which the straps on a walking brace are used to provide a firm grip around the leg, with the gel pads resiliently supporting the ankle.

DETAILED DESCRIPTION

Referring more particularly to the drawings, FIG. 1 is a cross-sectional view of an apparatus 12 for forming gel liners, illustrating certain principles of the invention. As shown, the apparatus includes a vacuum chamber 14 that is substantially enclosed, except at the bottom opening-channel 18 and the top opening. Vacuum chamber 14 is connected to a vacuum pump 16 using the channel 18. When the vacuum pump 16 is turned on, the air is drawn through channel 18, out of chamber 14. The opening at the top of the chamber 14 is substantially covered by a perforated plate base 20 having a number of drilled holes on its surface. In this manner, the vacuum created in the chamber 14, causes streams of air to flow into the chamber 14 through the fine holes 21 extending through the surface of the perforated plate base 20.

The apparatus also includes a spacer pad 22 which overlies the perforated base plate 20. Spacer pad 22 is relatively thin, and may have a thickness of about 3 millimeters. The spacer pad 22 may be made of rubber foam material. As shown in FIG. 3, the spacer pad 22 may have three patterned openings, each used for forming an individual and contiguous unit of gel-filled cushion pad. As shown in FIG. 1, a front aperture pad 24 overlies spacer pad 22. Normally, spacer pad 22 and the front pad 24 include substantially similar and aligned patterned openings on their surface. This is better illustrated in FIG. 3 showing substantially similar patterned openings on the surface of spacer pad 22 and front pad 24. Thus, by overlying front pad 24 on spacer pad 22 in such a way that the patterned opening of the front pad 24 and spacer pad 22 are in alignment, several "gel-pockets" or "gel-spaces" are formed, such as gel-pocket 27.

The gel-pocket 27 is enclosed laterally by the inner walls of front pad 24 and spacer pad 22. Further, as shown in FIG. 1, the front pad 24 has substantially the same thickness as that of the spacer pad 22. Of course, the two pads may have unequal thicknesses depending on the needs of a particular application. In addition, the front pad may also be formed of rubber foam material. A thin layer of a plastic or urethane film 26 is then laid over the front pad 24. Adhesive material is used to hold the thin film 26 over the front pad 24. With the vacuum pumps 16 being turned on, air will be sucked out of chamber 14 through channel 18. The displaced volume of air is replaced by the streams of air that flow into chamber 14 through the holes 21 extending through the perforated plate 20 adjacent the edges of the gel opening. The suction of air through openings 21 into chamber 14 causes the thin film 26 to be firmly drawn into contact with perforated plate 20 and conform to the inner walls of spacer pad 22 and front pad 24.

A heating device is then used to heat the thin film 26 so that thin film 26 will readily conform to the shape of the perforated base plate as well as to the inner walls of spacer pad 22 and front pad 24. However, a heating device is not necessary to conform the film. Gel-space 27 is formed by substantially conforming the thin film 26 to the shape of perforated base plate and the inner walls of front pad 24 and spacer pad 22. The vacuum pump 16 may continue to run in order to keep the thin film 26 in place. With thin film 26 kept tightly in place, a predetermined amount of liquid gel is then poured into the gel-space 27 to substantially fill up the gel-space. (See FIG. 2). The liquid gel is allowed to cool off to form a semi-solid and resilient gel pad layer.

FIG. 2 is a partial cross-sectional side view of apparatus 12 of FIG. 1, further illustrating the relative position of the gel pad with respect to the rest of the assembly. As shown in FIG. 2, the gel layer 28 substantially fills up the gel space 27. When the gel layer 28 solidifies within a short period of time, the depth of the gel layer 28 is substantially equal to the total thickness of spacer pad 22 and front pad 24. Then, the back pad 30 which may have adhesive material spread over its bottom surface, may be overlaid onto the thin film 26 and gel layer 28. The adhesive material causes the back pad 30 to firmly adhere to the urethane layer 26, sealing the gel material in the product formed by the urethane film and the back pad. At this point, the process of forming gel pads is substantially completed.

At this stage, the assembly includes multiple layers, namely, the back pad layer 30, the gel layer 28, the front pad layer 24, the urethane layer 26, and the spacer pad 22. All layers except for the spacer pad layer 22 are confined or tightly held together using adhesive material. More specifically, the front pad is adhesively secured to the urethane layer on one side of the urethane layer, and the back pad is adhesively secured to the other side of the urethane layer. Further, the semi-solid layer of gel 28 is confined between the urethane layer 26 on one side and to the back pad 30 on the other side. The spacer pad 22 is not connected to any of the other layers and may be left behind when the remainder of the assembly is lifted up, after the vacuum is released. The purpose of spacer pad 22 was to help form the gel-pocket for forming of the gel pad.

FIG. 3 is a top view of the intermediate product 50 that includes three contiguous units of gel pads. As shown in FIG. 3, three gel cushion pads, namely, cushion pads 34, 36 and 38 have been formed by the process described above. Obviously, the number of the contiguous gel pads may be increased by including more patterned openings on the surface of the spacer and front pads. Further, the pattern may be varied according to the needs of a particular application. The next step involves cutting out each individual unit so that they may be used individually in a walking brace. (See FIG. 4).

FIG. 4 is a top view of an individual gel liner unit 44 after it has been cut out of the composite pad 50 of FIG. 3. As shown in FIG. 4, the gel pad 42 is laterally enclosed by the inner walls of front aperture pad 40. With spacer pad 22 removed from the surface of unit 44, the surface of the gel layer 42 extends beyond the surface of front pad 40. This is better shown in FIGS. 5 and 6.

FIG. 5 is a cross-sectional view of the gel liner 44, viewed along the lines V—V of FIG. 4, illustrating the back pad 46, front aperture pad 40, and the semisolid gel layer 42. As clearly shown in FIG. 5, the gel layer 42 is thicker than front pad 40, as a result of the use of the spacer pad. This provides for a more efficient and comfortable gel pad that easily conforms to the shape of the ankle for a firm and resilient support of the injured ankle. These individual units of gel liners may easily be used in a walking brace 52 as shown in FIG. 7. Further, a portion of the gel pad 42 is laterally enclosed by the inner walls of the front aperture pad, to provide increased strength to the assembly. This is better shown in FIG. 6 of the drawings.

FIG. 6 is a side view of the gel liner 44 of FIG. 5, further illustrating the relative position of the different layers of the gel liner 44. As shown, a portion of the gel pad 42 is laterally confined by the inner walls of the front pad 40.

FIG. 7 is an exploded view of a walking brace 52 illustrating the manner in which the individual units of gel liners 44 and 54 are used in walking brace 52. Each of the gel pads 44 or 54 are used to provide for a resilient support against the ankle on each side of the leg. Gel liner 54 may be attached to the support wall 64 using velcro type material or other similar means. Similarly, gel liner 44 may be attached to the support wall 48 using Velcro type material or other similar means. The two gel pads 44 and 54 and the stiff support walls 48 and 64 each have two matching Velcro pads, see pads 65 and 67 on support wall 64, and pads 69 and 71 on gel pad unit 44. The gel pad units and the support walls may also have oppositely paired Velcro pads at their top and bottom so that the gel pads may not be mounted on the side walls upside down.

To further support the leg, a U-shaped stirrup member 80 is used. Stirrup member 80 includes a base plate or pad member 66 and straps 74 and 76. The base plate or pad member 66 extends underneath the heel of the user. The straps 74 and 76 are used for firmly attaching the base plate 66 to the side wall supports 64 and 48, respectively. Thus, for example, strap 76 extends in and out of slots 73 and 75, respectively and engages Velcro pad 77.

The side support walls 48 and 64 may better support the leg when a counter strap 72 is used just above the heel to further limit the side walls 64 and 48 from moving outward relative to the ankle. In addition, the bottom portion of the side walls 48 and 64 may be inserted in a shoe. With the bottom portion of the walking brace inserted in the shoe, the lace fastening loops 82 and 84 may be used to tightly secure the brace on the foot in the ankle area. This is done by passing the shoe lace through the D-shaped loop members 82 and 84 and then bringing the shoe laces back to the front and tying them together.

FIG. 8 illustrates the manner in which the walking brace is put on, with the gel pads providing a comfortable, firm and resilient support against the ankle. As shown, the liners 52 and 44 substantially conform to the shape of the leg. Further, the side support walls 64 and 48 provide for a firm support against the leg. The straps 68 and 70 are used to firmly hold the walking brace around the leg. This is better shown in FIG. 9.

FIG. 9 illustrates the manner in which a walking brace is secured. As shown, the upper part of the leg is firmly supported using the straps 68 and 70. The mid and lower portion of the leg is supported by strap 70 and counter strap 72. The lower portion of the leg is supported by the counter strap 72 and lace members 82, 84, and the U-shaped stirrup member 80.

The gel used in the implementation of the present invention is preferably of the type sold under the trademark ELASTO-GEL, by Southwest Technologies, Inc. of Kansas City, Mo. Attention is also directed to Edward I. Stout, U.S. Pat. No. 4,671,267, granted Aug. 1, 1986, which discloses the method for making the gel. In practice, the gel is mixed in liquid form and must be poured promptly into the pockets 27 for receiving gel as shown in FIG. 1 of the drawings, where it hardens to a semi-solid state within about 1 to 5 minutes. An open cell foam material may be located within the gel to prevent gel migration.

Concerning dimensions, the gel pad assemblies as shown in FIGS. 4, 5 and 6 may be in the order of ten or eleven inches in length and about 3 and one-half to 4 and one-half inches in width. The actual gel portion of the pad may be about three inches in width and about five inches in length. The pad unit as a whole is about one-quarter inch thick, with the gel portion protruding by about one-sixteenth inch. In one embodiment, the gel pad extends over most of the area of the unit of FIGS. 4, 5 and 6, with the front layer only forming a rim about one-quarter to one-half inch wide around the periphery. In another embodiment, no foam rubber layers were present in the unit; instead, a thicker spacer layer having a larger size opening was used, and a urethane film was used for the backing sheet. The resultant gel pad was similar in its overall configuration to the pads shown in my copending patent application cited hereinabove.

Concerning the gel pads, the combination of the inner gel pads and outer stiff supporting members, such as the plastic supports 48 and 64, or aluminum splinting stays, for example, has certain unique advantages. Specifically, these advantages include:

1. Hot and cold therapy resulting from the high specific heat or thermal capacity of the gel, and its resultant quality of being able to supply heat or cooling to an injured member, by pre-heating or pre-cooling the gel pad, before application.

2. Conformation of the gel pad to the user's bodily configuration. The gel pad has semi-solid gel which becomes deformed during use, and retains its deformed configuration to a substantial extent. Thus when a user takes the brace off, and then uses it again, putting it back on the ankle, wrist, or other part of the anatomy, the gel pad already conforms substantially to the shape of the anatomy and an immediate comfortable fit results.

3. The gel pad is self-sealing as compared with air-inflatable cushion arrangements, so that injury from the stiff supporting members cutting or rubbing the user, cannot occur.

4. The gel is not U.V. sensitive, and therefore does not deteriorate when subject to prolonged U.V. exposure.

It is noted in passing that the invention is not limited to the embodiment shown in the drawings or to the foregoing detailed description. By way of example and not of limitation, the spacer pad, front pad, and back pad may be made of flexible foam rubber material, or other flexible material. Alternatively, the spacer pad may be made of solid and inflexible material. The thickness of these pads may be relatively small, for example 3 millimeters. The thickness of the three pads may be substantial equal or may be different. The back pad or rear closure may be very thin and made of flexible material. For example, the backing layer may be made of a thin plastic film, such as the urethane film 26, and the two urethane films may then be heat bonded or adhesively sealed to one-another to confine the gel. When the gel pad is confined by urethane film, front and back, a thicker spacer pad may be used so that the gel pad remains fairly thick, and may have no front pad. Apertures may have various patterns to meet the needs of a particular application. The apertures may have a definite geometrical shape, for example, a rectangular shape, a horseshoe shape, or they may have curved boundaries to match the desired orthopaedic soft goods application. The thin film may be made of urethane or other suitable thin and flexible material. The vacuum chamber may be wooden, plastic or may be made of other suitable material. The holes on the perforated base plate may be substantially equal in size ranging from less than one to more than five millimeters in diameter. The holes may have uneven diameter sizes. Further, the holes may be evenly distributed throughout the base plate, or preferably, they may outline the inner edge of the spacer pad openings, with different perforated base plates being employed for differently shaped gel pads. The pattern on the surface of each of the pads may vary according to particular needs of an application.

What is claimed is:

1. A method for forming orthopaedic gel pad assemblies using a substantially flat perforated base plate with a vacuum chamber comprising the steps of:
    placing a spacer pad over the base plate with at least one patterned opening through the spacer pad conforming to the desired shape of the gel pad, with drilled holes in the base plate communicating between said patterned opening and the vacuum chamber
    placing an apertured front pad over the spacer pad with a patterned opening through the front pad aligned with the patterned opening of the spacer pad;
    applying an adhesive coating to the upper surface of the front pad;
    placing a thin flexible plastic film or sheet over the adhesive coated surface of the front pad;
    drawing air through holes in the substantially flat base plate for exerting force on the plastic film and pulling the film down into the opening and in engagement with said substantially flat plate;
    pouring a measured quantity of liquid gel into said patterned opening;
    letting the gel harden to a semi-solid state;
    placing a backing layer on top of the plastic sheet, with the plastic sheet being adhered to the backing layer, to confine the gel into the resultant pocket with no gel exposed, to protect the gel from contamination;
    separating the front pad, the confined gel and the backing layer from the spacer pad and the base plate; and
    cutting the layers around the confined gel to form an orthopaedic gel assembly with the gel pad protruding from the front pad thereof by a distance equal to the thickness of the spacer pad.

2. A method for forming orthopaedic gel cushion pads as defined in claim 1 wherein open cell foam material is located in the liquid gel to prevent gel migration.

3. A method as defined in claim 1 wherein the spacer pad includes a layer of foam rubber.

4. A method as defined in claim 1 wherein the openings in the aperture front pad correspond substantially with the openings on the spacer pad.

5. A method as defined in claim wherein the apertured front pad includes a layer of foam rubber.

6. A method as defined in claim 1 wherein said base plate includes a multitude of drilled holes on its surface spaced along the inside of said openings to insure conformance of the film to the shape of the opening.

7. A method as defined in claim 1 wherein said spacer pad and backing pad include a layer of foam rubber.

8. A method as defined in claim 1 wherein said spacer pad, front pad and back pad have substantially equal thickness.

9. A method as defined in claim 1 wherein the patterned opening on the surface of said spacer pad is substantially identical in configuration to the patterned opening on the surface of said front pad.

10. A general purpose method for forming substantially flat orthopaedic gel pads of any desired peripheral configuration and thickness using a flat perforated base plate with a vacuum chamber comprising the steps of:
   placing a spacer pad over the base plate, with a patterned opening through the spacer pad and having the desired configuration of the gel pads, and with a plurality of drilled holes in the base plate communicating with the patterned opening;
   placing a thin flexible plastic film or sheet over and extending down into the opening in the spacer pad;
   drawing air through holes in the base plate for exerting force on the plastic film and pulling the film down into the opening and in engagement with said plate;
   pouring a measured quantity of liquid gel into said patterned opening;
   letting the gel harden to a semi-solid state;
   placing a backing layer on top of the plastic sheet;
   securing the backing layer to said plastic sheet to confine the gel into the resultant pocket and to seal the gel against contamination;
   removing the plastic sheet, the gel and the backing layer from the spacer pad; and
   cutting the layers around the confined gel to form an orthopaedic gel pad;
   whereby any desired gel pad peripheral configuration may be formed using the same perforated base plate and vacuum chamber, using spacers having differently shaped openings.

11. A method for forming orthopaedic gel pad assemblies using a substantially flat perforated base plate with a vacuum chamber comprising the steps of:
   placing a spacer pad over the base plate with a plurality of patterned openings through the spacer pad conforming to the desired shape of the gel pad, with drilled holes in the base plate communicating between said patterned opening and the vacuum chamber;
   placing an apertured front pad over the spacer pad with patterned openings through the front pad aligned with the patterned openings of the spacer pad;
   applying an adhesive coating to the upper surface of the front pad;
   placing a thin flexible plastic film or sheet over the adhesive coated surface of the front pad;
   drawing air through holes in the substantially flat base plate for exerting force on the plastic film and pulling the film down into the opening and in engagement with said substantially flat plate;
   pouring a measured quantity of liquid gel into said patterned openings;
   letting the gel harden to a semi-solid state;
   placing a backing layer on top of the plastic sheet, with the plastic sheet, being adhered to the backing layer, to confine the gel into the resultant pockets with no gel exposed, to protect the gel from contamination;
   separating the front pad, the confined gel and the backing layer from the spacer pad and the base plate; and
   cutting the layers around the confined gel to form an orthopaedic gel pad assemblies, with the gel pad protruding from the front thereof by a distance equal to the thickness of the spacer pad.

12. A general purpose method for forming substantially flat orthopaedic gel pad assemblies, of any desired peripheral configuration and thickness, using a flat perforated base plate with a vacuum chamber, comprising the steps of:
   placing a spacer pad over the base plate, with a plurality of patterned openings through the spacer pad having the desired peripheral configuration of the gel pads, and with a plurality of drilled holes in the base plate communicating between said patterned openings and the vacuum chamber;
   placing a thin flexible plastic film or sheet over and extending down into the openings in the spacer pad;
   drawing air through holes in the base plate for exerting force on the plastic film and pulling the film down into the openings and in engagement with said plate;
   pouring a measured quantity of liquid gel into said patterned openings;
   letting the gel harden to a semi-solid state;
   placing a backing layer on top of the plastic sheet;
   securing the backing layer to said plastic sheet to confine the gel into the resultant pockets and to seal the gel against contamination;
   removing the thin film, the gel and the backing layer from the spacer pad; and
   cutting the layers around the confined gel to form a plurality of orthopaedic gel pad assemblies;
   whereby any desired gel pad peripheral configuration and thickness may be formed using the same substantially perforated base plate and vacuum chamber, using spacer pads having shaped openings of the desired configuration, and spacer pads of the desired thickness.

13. A method as defined in claim 1 wherein a plurality of said gel pad assemblies are formed concurrently.

14. A method as defined in claim 1 wherein said front pad and said backing layer are formed of foam rubber in sheet form.

15. A method as defined in claim 10 wherein said backing layer is formed of foam rubber in sheet form.

16. A method as defined in claim 11 wherein said front pad and said backing layer are formed of foam rubber in sheet form.

17. A method as defined in claim 12 wherein said backing layer is formed of foam rubber in sheet form.

* * * * *